(12) United States Patent
Völker

(10) Patent No.: US 8,460,544 B2
(45) Date of Patent: Jun. 11, 2013

(54) SUPPLY DEVICE FOR DIALYSIS APPARATUSES

(76) Inventor: Manfred Völker, Blankenbach (DE)

(*) Notice: Subject to any disclaimer, the term of this patent is extended or adjusted under 35 U.S.C. 154(b) by 380 days.

(21) Appl. No.: 12/857,627

(22) Filed: Aug. 17, 2010

(65) Prior Publication Data

US 2011/0041928 A1 Feb. 24, 2011

(30) Foreign Application Priority Data

Aug. 22, 2009 (DE) .......................... 10 2009 038 571

(51) Int. Cl.
*B01D 61/26* (2006.01)
(52) U.S. Cl.
USPC ........ 210/247; 210/232; 210/248; 210/257.1; 210/321.71
(58) Field of Classification Search
USPC ................. 210/232, 233, 237, 238, 240, 247, 210/248, 257.1, 261, 321.71; 137/240, 561 R
See application file for complete search history.

(56) References Cited

U.S. PATENT DOCUMENTS

| | | | |
|---|---|---|---|
| 4,063,663 A * | 12/1977 | Larson et al. ................... | 222/52 |
| 8,048,209 B2 * | 11/2011 | Dannenmaier et al. ............. | 96/6 |
| 8,206,580 B2 * | 6/2012 | Dannenmaier et al. ....... | 210/188 |
| 2009/0178968 A1 * | 7/2009 | Cummins .................. | 210/221.2 |

* cited by examiner

*Primary Examiner* — John Kim
(74) *Attorney, Agent, or Firm* — Hammer & Associates, P.C.

(57) ABSTRACT

The supply device for dialysis apparatuses, comprising a permeate line and at least one concentrate line for supplying permeate and dialysis concentrate(s) to a dialysis apparatus to be mixed so as to obtain dialysis liquid, and comprising a waste water line for discharging waste water out of the dialysis apparatus, is characterized in that the waste water line is in communication with a substantially funnel-shaped outlet container into which the waste water falls in a free fall, thereby impinging on an inclined wall section of the outlet container. Virtually no noise is created that would be noticed by a patient, and a pivotable door is preferably arranged at the outlet container for permitting the taking of samples in an easy way from the outlet container by means of small test rods.

8 Claims, 3 Drawing Sheets

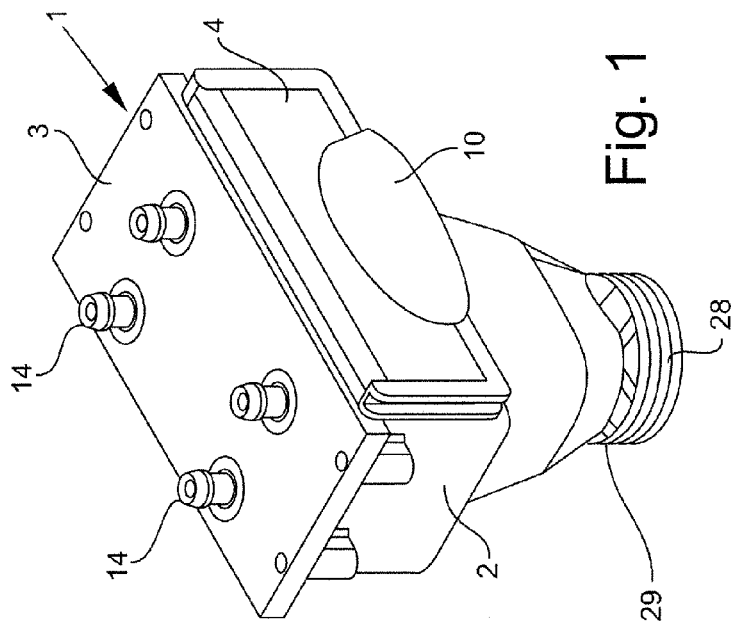
Fig. 1
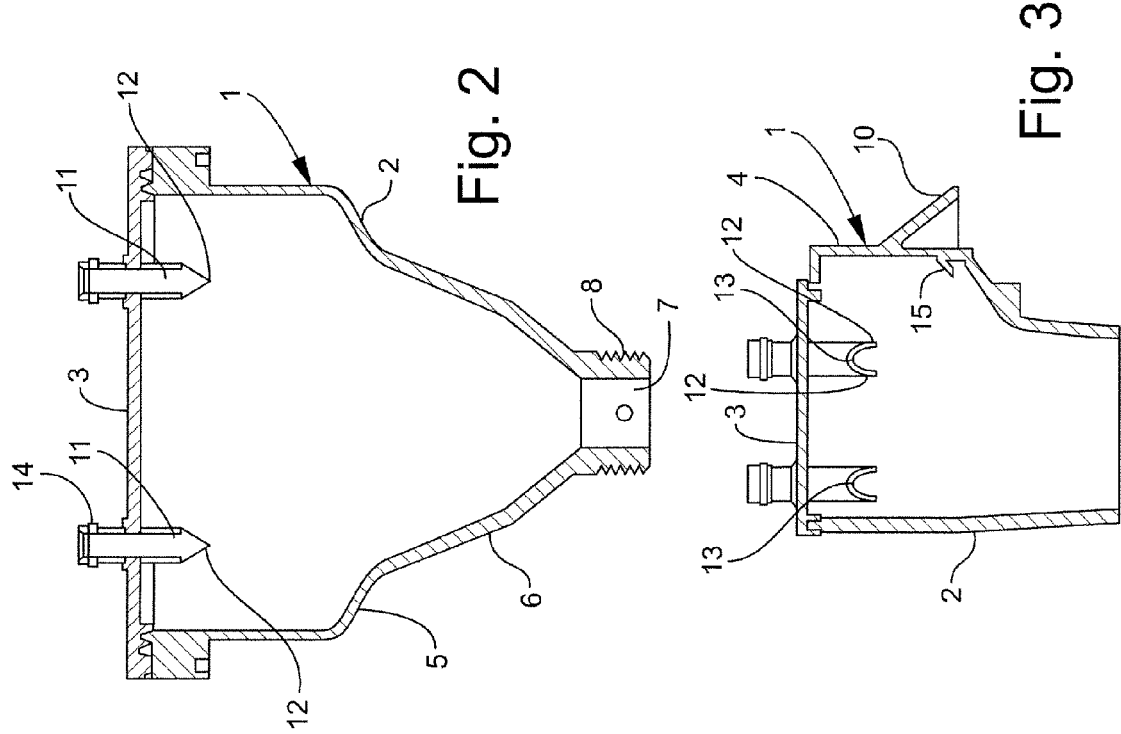
Fig. 2
Fig. 3

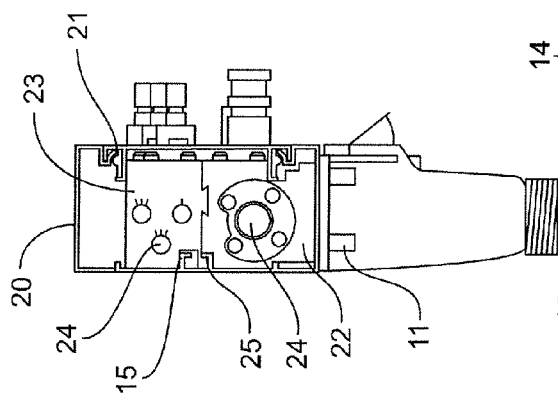
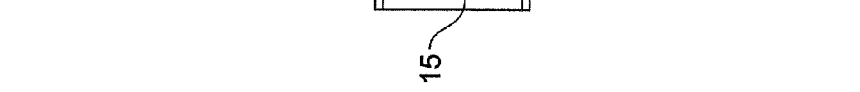
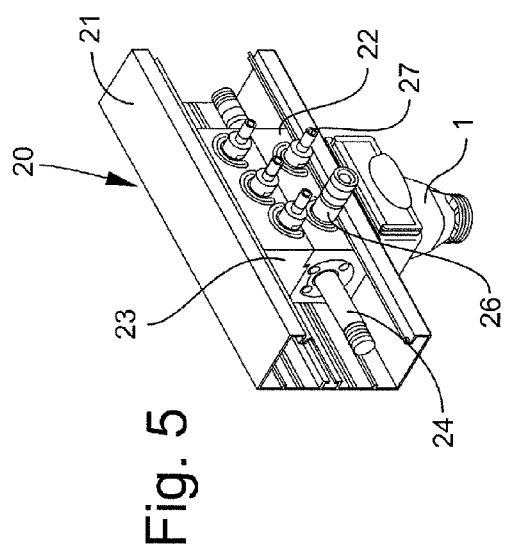
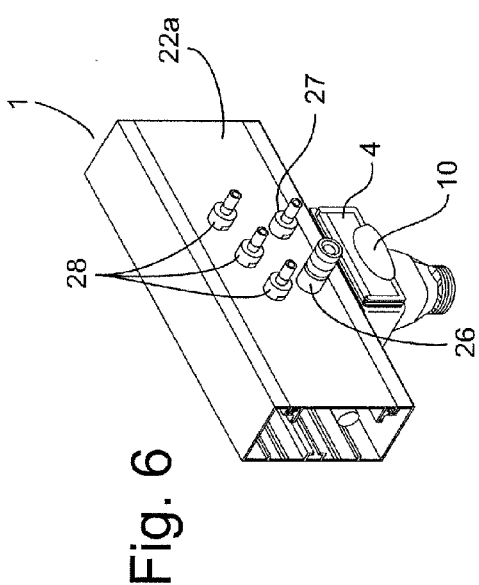

SUPPLY DEVICE FOR DIALYSIS APPARATUSES

The present invention relates to a hydraulic supply device for dialysis apparatuses, the device comprising a permeate line and at least one concentrate line for supplying permeate and dialysis concentrate(s) to a dialysis apparatus to be mixed at that place so as to obtain dialysis liquid, and comprising a waste water line for discharging waste water out of the dialysis apparatus, the waste water being discharged into a drain.

The permeate line passes permeate produced by a reverse osmosis device to a plurality of series-connected dialysis apparatuses which are further fed via at least one concentrate line, mostly three concentrate lines—either via three coupling means or via a concentrate selection switch, with concentrate; together with the permeate the concentrate is preferably mixed in the respective dialysis apparatuses to obtain dialysis liquid and is fed to the dialyzer from which dialysis liquid enriched with urea etc., here generally designated as waste water, is discharged out of the dialysis apparatus and supplied to a drain.

A conventional waste-water outlet has serious drawbacks: it sprays and splashes, which is a real noise nuisance for the patients, it has an unpleasant odor and is unhygienic, it tends to form residues, and it is difficult to take a sample in the form of small paper-like rods, e.g. for testing chemical residues after disinfection of the connected apparatus with the help of small test rods.

Under a first aspect it is the object of the present invention to find a better solution for the waste-water outlet, the solution eliminating the above drawbacks either completely or at least in part.

The conventional feeding of dialysis apparatuses via a permeate line and at least one concentrate line requires great installation efforts and is thus expensive when the lines are e.g. mounted on the wall of a room and are concealed for optical reasons by wall sections arranged in front thereof. This also requires a lot of space.

Under a further aspect it is the object of the present invention to indicate a compact and inexpensive supply device that can be installed easily.

Under the first aspect of the invention it is intended that the waste-water line leads to a substantially funnel-shaped outlet container into which the waste water falls in a free fall, thereby impinging on an inclined wall section of the outlet container. The angle of the at least one inclined wall section relative to the horizontal should here be at least 45°.

The free outflow of the waste water into the funnel-shaped container reliably prevents back-contamination of the wastewater line from the drain.

Since the waste water impinges in a free fall on an associated inclined wall section of the outlet container, virtually no noise is created that would be noticed by the patients, which is supported by the fact that the outlet container is preferably composed of a funnel, an upper lid and a pivotable door to form a closed housing. The pivotable door which is preferably arranged in a sidewall of the outlet container and is normally closed makes it possible to take a sample from the outlet container by means of small test rods without any difficulties. The otherwise closed housing reliably prevents the exit of unpleasant odors into the patient's room.

It is suggested with particular advantage that at least one waste-water inlet nozzle projecting into the interior of the outlet container is passed through the lid of the outlet container. It is here also possible to provide a plurality of wastewater inlet nozzles, e.g. four nozzles, which are connected to the waste-water lines of different apparatuses.

Furthermore, it is suggested that each waste-water inlet nozzle should have a lower rim shaped in such a way that the waste-water jet exits smoothly in vertical direction, substantially without any swirl, downwards out of the inlet nozzle, i.e. also without any swirl if there is only a small flow rate through the inlet nozzle. To this end it is suggested that the lower rim section of the inlet nozzle should have at least one pointed projection. Preferably, two diametrically opposed pointed projections are provided and the rim section of the inlet nozzle extends between the two projections in a concave curvature. This creates a smooth jet so that the freely falling waste water reliably impinges on the inclined wall section(s) arranged underneath the inlet nozzles. This creates a virtually noiseless outflow of the waste water.

The funnel is preferably an injection molded part of plastic, just like the lid and the door which is pivotable about an upper horizontal axis. A thread onto which a drain pipe or a flexible drain hose can be screwed can be formed on the lower end portion of the funnel on the outside. In the interior of the lower end portion, webs can extend over the cross section, and a siphon cleaning tablet which can be introduced through the opened door can be placed on said webs.

The funnel consists expediently of an upper square section having one longitudinal wall that is formed by the pivotable door, and of a lower section which is constricted with inclined transition and is substantially funnel-shaped and on the inclined walls of which the falling waste water is mainly impinging. Instead of the lower thread, it is also possible to provide a lower plug-type connection for fastening to an extending standard pipe or hose line or a siphon. The funnel is optically appealing and has inner wall sections smoothly passing into one another, on which residues can hardly deposit, whereby the outlet container is very hygienic.

Under a further aspect of the present invention at least one permeate block is inserted into the permeate line while at least one concentrate block or concentrate selection switch is inserted into the concentrate lines in a corresponding way. These two blocks are advantageously made of plastics and have the associated bores to form sections of the permeate line and of the concentrate lines. A permeate block and a concentrate block may be provided for each dialysis apparatus. The blocks may here also be configured to be longer so as to feed e.g. a plurality of dialysis apparatuses in a room for patients.

All of the permeate blocks and concentrate blocks are provided on their front sides with supply connections that should be designed as hose nozzle connections or plug connections, and coupling means or hose connections branch off from their longitudinal bores to the connection of the hoses leading to the dialysis apparatuses.

It is further suggested with great advantage that the permeate line, the concentrate lines as well as the permeate blocks and concentrate blocks are arranged in a supply channel from the sidewall of which the coupling means and the connections for the hydraulic supply lines are projecting. This supply line is expediently shaped in the form of a rectangular cross-section and is preferably composed of an approximately C-shaped channel element and of a flat sidewall from which the connections for the dialysis apparatus are projecting. The supply channel, however, may also have a different shape adapted to the installation and connection demands. This supply channel may e.g. be fastened to a room wall where it can hardly be seen, or it may be held on racks near the dialysis apparatuses. It is just as well possible to mount the supply channel on a pivot arm fastened to the wall so as to comply with the hygienic and spatial requirements in an even better way. A vertical or horizontal installation of the supply unit is here possible.

The permeate blocks and the concentrate blocks are advantageously arranged in pairs one on top of the other in the supply channel, thereby engaging each other with dovetail-shaped sections. Instead of the one concentrate block with up to three concentrate connections, it is possible to integrate a concentrate selection switch which enables the user to select the respectively needed concentrate for the dialysis apparatus in a simple way without any re-coupling operations.

Furthermore, it is suggested that the lid of the funnel should be mounted on the bottom side of the supply channel, with the waste-water inlet nozzles projecting into the interior of the supply channel, and that the permeate block should comprise at least one waste-water line bore separated from the permeate bore with a waste-water coupling means leading through the sidewall of the channel, with the waste-water line bore being connected to the at least one waste-water inlet nozzle.

The above-described hydraulic supply device can moreover be combined with a channel expediently positioned next to or above the device for the electrical supply and communication of the consumer.

The supply device according to the invention can be produced at low costs and can be installed with small efforts. It has an appealing appearance and need thus not be concealed in a patient's room by panels arranged in front of the device.

Further details of the invention become apparent from the following description of a preferred embodiment of the waste-water outlet container and a supply module.

BRIEF DESCRIPTION OF THE DRAWINGS

FIG. 1 is a perspective view of a waste-water outlet container;

FIG. 2 is a longitudinal section taken through the container of FIG. 1;

FIG. 3 is a cross section taken through the upper part of the container of FIG. 1;

FIG. 4 is a partly cut side view of the waste-water outlet container with a wall mounting member;

FIG. 5 is a perspective view of a supply module with outlet container with remote front channel wall;

FIG. 6 is a view similar to FIG. 5, but with laterally connected channel;

FIG. 7 is a vertical section taken through the supply module according to FIG. 6.

FIGS. 1 to 4 show an outlet container 1 in which the waste water from a dialysis apparatus (not shown) is supplied to a drain. The outlet container 1 is composed of three container parts, namely a funnel 2, a lid 3 closing the upper side of the funnel 2, and a hinged door 4 which is outwardly pivotable about an upper longitudinal axis. These three container parts are made from plastics in an injection molding process.

Figure 8:
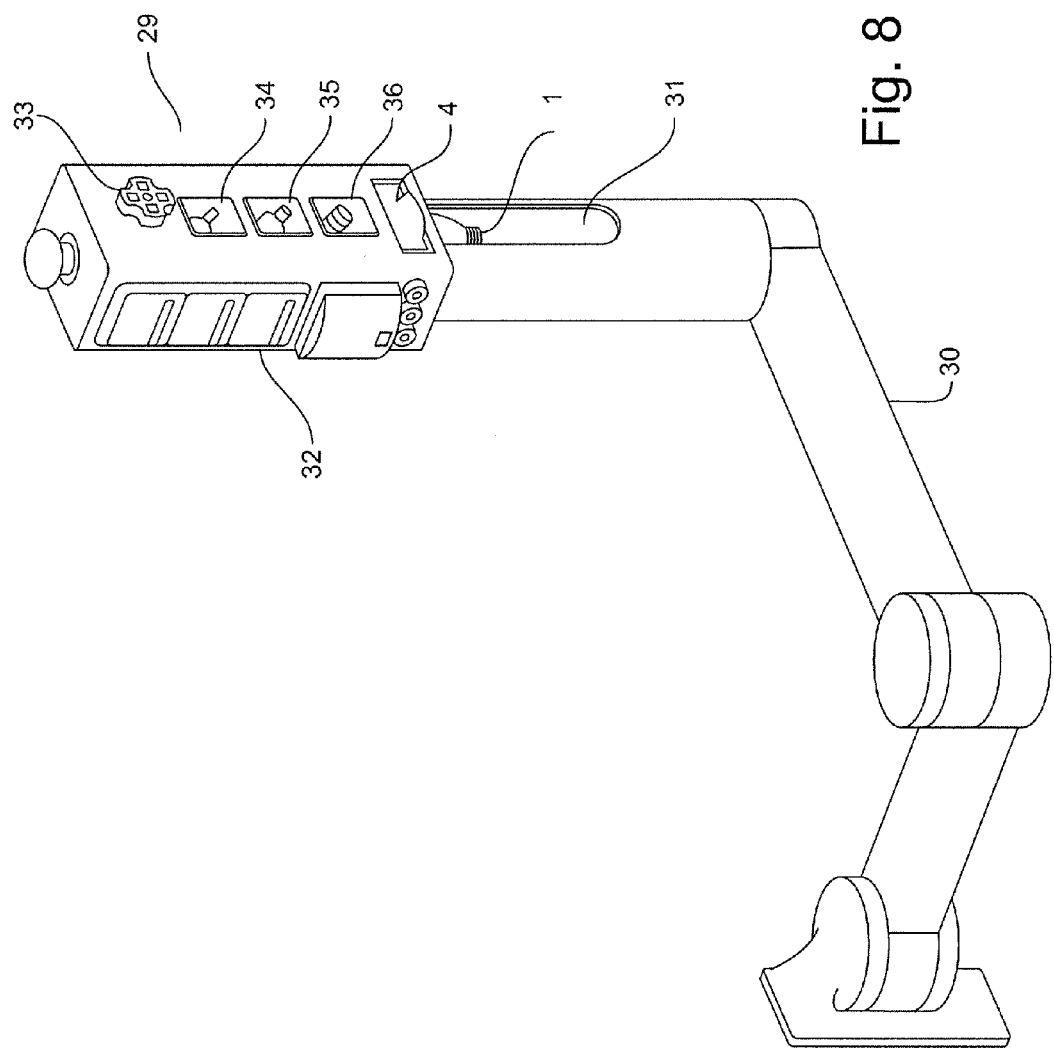
FIG. 8 shows a supply module fastened to a hinged arm.

The funnel 2 has an upper, substantially square section, with one of its longitudinal walls forming the door 4. The square section passes via inwardly extending wall sections 5 into the approximately funnel-shaped lower section 6 that narrows down towards the lower end in slopes having an inclination relative to the horizontal of more than 45°. The lower cylindrical end section 7 is provided with an external thread 8 onto which a standard drain pipe can be screwed.

The door 4 includes hinge balls 9 which are formed on the upper lateral ends of the door and which lock into associated holes of the funnel wall so that the door 4 can be comfortably pivoted upwards on a molded-on handle 10. For instance, a siphon cleaning tablet can thereby be placed on webs (not shown) that bridge the lower end section 7 in the form of a star, or small test rods can be introduced into the interior of the outlet container.

The transitions of the individual wall sections are smoothly rounded, so that virtually no deposits can settle on the inner walls.

Four waste-water inlet nozzles that end inside the outlet container 1 in a special rim contour, namely two diametrically opposite peaks 12 and interposed concave cut-outs 13, extend through the lid 3. This configuration accomplishes a smooth liquid jet without any swirl even in the case of a small water flow rate, so that the waste water impinges in a reliable and smooth manner on the inclined wall of the funnel-shaped section 6 of the outlet container 1 and flows off virtually without any noise. The waste-water inlet nozzles 11 are provided with hose nozzle connections 14 on the top side of the lid 3. Constrictions for receiving sealing rings are additionally introduced into the hose nozzle connections.

An inwardly projecting drip edge 15 is formed on the lower end section of the door 4 for discharging condensation water.

As shown in FIG. 4, a wall mounting member 15 can be provided on the outlet container 1. The lid 3 is fastened to the funnel body 2 with fastening screws 16, which are screwed into threaded nuts seated in threaded-nut receiving means 17. This figure also illustrates a groove 18 for the front frame installation and one of the two lateral holes 19 for the engagement of the hinge balls 9.

FIGS. 5 to 7 show a supply channel 20 which accommodates a permeate line and concentrate lines for the supply of connected dialysis apparatuses. The supply channel 20 is composed of an essentially C-shaped channel section 21 and a flat side section 22 to form a closed rectangle.

The figures show a permeate block 22 and a concentrate block 23 which are inserted into the permeate line and the concentrate lines. To this end permeate supply connections 24 are provided on the front sides of the permeate block 22 and concentrate supply connections 24 are disposed on the front sides of the concentrate block 23. The permeate block 22 and the concentrate block 23 consist of substantially square plastic blocks with corresponding continuous bores, with the two blocks 22 and 23 being put together by a dovetail joint 25.

The permeate block 22 additionally contains a waste-water bore which extends in a way separated from the permeate bore and in which a waste-water coupling means 26 ends at the side. The lid 3 of the outlet container 1 is fastened to the bottom side of the channel 20, its inlet nozzles 14 being in communication with the waste-water bore of the permeate block 22.

The permeate bore which extends in the longitudinal direction through the permeate block 22 communicates with a permeate coupling means 27 while concentrate coupling means 28 communicate with the bores of the concentrate block 23. Hoses leading to the respective dialysis apparatus are connectable to these coupling means.

FIG. 8 illustrates a supply module 29 which is held by a hinged arm 30 that may e.g. be fastened to the wall of a patient's room. In comparison with FIGS. 5 to 7 the concentrate coupling means 28 have been replaced by a concentrate selection switch 33. Both the permeate coupling means 27 and the concentrate coupling means 28 are in this embodiment directly coupled to the dialysis apparatus. The illustrated coupling positions 34, 35, 36 are used in the disconnected state of the dialysis apparatus as a parking station for the free coupling means.

An outlet container 1 having a bottom side accessible through a slit 31 in the fastening arm 30 projects from the bottom side of the module 29. The supply hoses leading to the module 29 can extend through the interior of the hinged arm 30. The supply module 29 is arranged for an associated dialysis apparatus in the vicinity thereof.

Electrical lines may additionally be included with switches 32 etc. arranged on a further outer wall of the module 29.

The invention claimed is:

1. A supply device for dialysis apparatuses, comprising a permeate coupling means (27) and at least one concentrate coupling means (28) for supplying permeate and dialysis concentrate(s) to a dialysis apparatus to be mixed so as to obtain dialysis liquid, and comprising a waste water coupling means (26) for discharging waste water out of the dialysis apparatus, characterized in that the waste water coupling means (26) is in communication with a substantially funnel-shaped outlet container (1) in which the waste water falls in a free fall, thereby impinging on an inclined wall section (6) of the outlet container (1) and wherein the outlet container (1) is composed of a funnel (2), an upper lid (3) and a pivotable door (4).

2. The supply device according to claim 1, characterized in that at least one waster-water inlet nozzle (11) passes through the lid (3).

3. The supply device according to claim 2, characterized in that the at least one waste-water inlet nozzle (11) comprises a lower rim section with at least one pointed projection (12).

4. The supply device according to claim 3, characterized in that the rim section comprises two opposite pointed projections (12) between which the rim section ends in concave rim edges (13).

5. The supply device according to claim 1 further comprising at least one permeate block (22) and at least one concentrate block (23) that comprise the associated bores.

6. The supply device according to claim 5, characterized in that all permeate blocks (22) and all concentrate blocks (23) are provided with supply connections (24) configured as hose-nozzle or plug-type connections, and with coupling means (26, 27, 28).

7. The supply device according to claim 5, characterized in that the permeate coupling means (27), the concentrate coupling means (28) as well as the permeate blocks (22) and concentrate blocks (23) are arranged in a supply channel (20) from the sidewall (22a) of which the coupling means (26, 27, 28) are projecting.

8. The supply device according to claim 7, characterized in that the lid (3) of the outlet container (1) is mounted on the bottom side of the supply channel (20), and that the permeate block (22) comprises at least one separate waste-water line bore with a waste-water coupling means (26) passing through the sidewall (22a) of the channel, with the waste-water line bore being connected to the at least one waste-water inlet nozzle (11).

* * * * *